(12) United States Patent
Gatzemeyer et al.

(10) Patent No.: US 7,137,163 B2
(45) Date of Patent: *Nov. 21, 2006

(54) POWER TOOTHBRUSH AND POWER SOURCE

(75) Inventors: John J. Gatzemeyer, Hillsborough, NJ (US); Henry Goldfine, Edison, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/260,586

(22) Filed: Sep. 27, 2002

(65) Prior Publication Data

US 2004/0060136 A1  Apr. 1, 2004

(51) Int. Cl.
*A61C 17/22* (2006.01)

(52) U.S. Cl. ............................. 15/22.1; 15/28; 15/110; 15/188; 601/142

(58) Field of Classification Search .............. 15/22.1, 15/28, 22.2, 22.4, 29, 110, 167.1, 188; 601/142, 601/139, 140, 141
See application file for complete search history.

(56) References Cited

U.S. PATENT DOCUMENTS

| | | | |
|---|---|---|---|
| 411,910 A | 10/1889 | Van Horne |
| 1,006,630 A | 10/1911 | Clarke |
| 1,128,139 A | 2/1915 | Hoffman |
| 1,142,698 A | 6/1915 | Crumbaugh |
| 1,188,823 A | 6/1916 | Plank |
| 1,191,556 A | 7/1916 | Blake |
| 1,267,039 A | 5/1918 | Akin |
| 1,268,544 A | 6/1918 | Cates |
| 1,526,267 A | 2/1925 | Dessau |
| 1,588,785 A | 6/1926 | Van Sant |
| 1,598,224 A | 8/1926 | Van Sant |
| 1,720,017 A * | 7/1929 | Touchstone .................. 15/180 |
| 1,833,555 A | 11/1931 | Bell et al. |
| 1,872,832 A | 8/1932 | Silverberg |
| 1,910,414 A | 5/1933 | Varga |
| 1,924,152 A | 8/1933 | Coney et al. |
| 2,059,914 A | 11/1936 | Rosenberg |
| 2,088,839 A | 8/1937 | Coney et al. |
| 2,117,174 A | 5/1938 | Jones |
| 2,139,245 A * | 12/1938 | Ogden ......................... 601/139 |
| 2,248,525 A * | 7/1941 | Fleissner .................... 601/137 |
| 2,290,894 A | 7/1942 | Rivanov |
| 2,443,461 A | 6/1948 | Kempster |
| 2,545,814 A | 3/1951 | Kempster |
| 2,637,870 A | 5/1953 | Cohen |
| 2,686,325 A | 8/1954 | Silver |
| 2,702,914 A | 3/1955 | Kittle et al. |
| 2,706,825 A * | 4/1955 | Blakeman .................. 15/176.4 |

(Continued)

FOREIGN PATENT DOCUMENTS

DE        200 02 885 U1    4/2001

(Continued)

*Primary Examiner*—Mark Spisich
(74) *Attorney, Agent, or Firm*—Ellen K. Park

(57) ABSTRACT

A powered toothbrush is provided and includes a handle portion having a neck formed at one end and a head coupled to the neck. The handle portion is adapted to receive a single battery therein in a tight fitting arrangement. The head includes a base, and one or more carriers coupled to the base. At least one of the carriers is operatively connected to a drive for moving the one or more coupled carriers in respective directions. The one or more carriers have bristles, elastomeric cleaning members, or a combination thereof extending outwardly therefrom.

28 Claims, 8 Drawing Sheets

U.S. PATENT DOCUMENTS

| | | | |
|---|---|---|---|
| 2,777,145 A | | 1/1957 | Krieger et al. |
| 3,103,027 A | | 9/1963 | Birch |
| 3,261,354 A | | 7/1966 | Shpuntoff |
| 3,641,610 A | | 2/1972 | Lewis, Jr. |
| 4,277,862 A | | 7/1981 | Weideman |
| 4,493,125 A | | 1/1985 | Collis |
| 4,827,551 A | * | 5/1989 | Maser et al. ............... 15/24 |
| 4,929,180 A | | 5/1990 | Moreschini |
| 5,170,525 A | | 12/1992 | Cafaro |
| 5,341,537 A | | 8/1994 | Curtis et al. |
| 5,348,473 A | | 9/1994 | Kivlighan, Jr. |
| 5,446,940 A | | 9/1995 | Curtis et al. |
| 5,524,312 A | | 6/1996 | Tan et al. |
| 5,584,690 A | | 12/1996 | Maassarani |
| 5,604,951 A | | 2/1997 | Shipp |
| 5,617,603 A | | 4/1997 | Mei |
| 5,625,916 A | | 5/1997 | McDougall |
| 5,628,082 A | | 5/1997 | Moskovich |
| 5,669,097 A | | 9/1997 | Klinkhammer |
| 5,735,011 A | | 4/1998 | Asher |
| 5,802,656 A | | 9/1998 | Dawson et al. |
| 5,809,608 A | | 9/1998 | Zadro |
| 5,810,856 A | | 9/1998 | Tveras |
| 5,896,614 A | | 4/1999 | Flewitt |
| 5,930,860 A | | 8/1999 | Shipp |
| 5,930,861 A | | 8/1999 | White |
| 6,000,083 A | * | 12/1999 | Blaustein et al. ............... 15/28 |
| 6,041,467 A | | 3/2000 | Roberts et al. |
| 6,105,191 A | | 8/2000 | Chen et al. |
| 6,119,296 A | | 9/2000 | Noe et al. |
| 6,148,462 A | | 11/2000 | Zseng |
| 6,276,021 B1 | | 8/2001 | Hohlbein |
| 6,311,358 B1 | | 11/2001 | Soetewey et al. |
| 6,319,332 B1 | | 11/2001 | Gavney, Jr. et al. |
| 6,374,448 B1 | | 4/2002 | Seifert |
| 6,389,634 B1 | | 5/2002 | Devlin et al. |
| 6,446,295 B1 | * | 9/2002 | Calabrese ............... 15/28 |
| 6,463,618 B1 | | 10/2002 | Zimmer |
| 6,463,619 B1 | | 10/2002 | Gavney, Jr. |
| 6,513,182 B1 | * | 2/2003 | Calabrese et al. ............ 15/110 |
| 6,571,417 B1 | | 6/2003 | Gavney, Jr. et al. |
| 6,658,688 B1 | | 12/2003 | Gavney, Jr. |
| 6,725,490 B1 | * | 4/2004 | Blaustein et al. ............ 15/22.2 |
| 2001/0039889 A1 | | 11/2001 | Gavney, Jr. |
| 2003/0019060 A1 | | 1/2003 | Gavney, Jr. |
| 2003/0033680 A1 | * | 2/2003 | Davies et al. ............... 15/22.1 |
| 2003/0084525 A1 | | 5/2003 | Balustein et al. |
| 2003/0140437 A1 | | 7/2003 | Eliav et al. |
| 2003/0182744 A1 | | 10/2003 | Fattori et al. |
| 2004/0060134 A1 | | 4/2004 | Eliav et al. |

FOREIGN PATENT DOCUMENTS

| | | | |
|---|---|---|---|
| EP | 0 449 655 B1 | | 3/1991 |
| EP | 1 350 442 A1 | | 10/2003 |
| FR | 561498 | | 10/1923 |
| GB | 297994 | | 10/1928 |
| GB | 2 040 161 A | | 1/1980 |
| GB | 2319170 | * | 5/1998 |
| GB | 2371217 | * | 7/2002 |
| JP | 9-140456 | * | 6/1997 |
| JP | 182626 | | 7/1997 |
| WO | WO 81/00804 | | 9/1980 |
| WO | WO 95/07036 | | 3/1995 |
| WO | WO 96/20654 | | 12/1995 |
| WO | WO 96/15696 | | 5/1996 |
| WO | WO 96/28994 | | 9/1996 |
| WO | WO 98/18364 | | 5/1998 |
| WO | WO 98/22000 | | 5/1998 |
| WO | WO 98/48662 | | 11/1998 |
| WO | WO 99/01054 | | 1/1999 |
| WO | WO 99/07251 | | 2/1999 |
| WO | WO 99/37181 | | 7/1999 |
| WO | WO 99/37182 | | 7/1999 |
| WO | WO 00/64307 | | 11/2000 |
| WO | WO 00/76369 A2 | | 12/2000 |
| WO | WO 01/01817 A1 | | 1/2001 |
| WO | WO 01/21036 A1 | | 3/2001 |
| WO | WO 01/26505 A1 | | 4/2001 |
| WO | WO 02/05725 A1 | | 1/2002 |
| WO | WO 02/11583 A2 | | 2/2002 |
| WO | WO 02/19866 A1 | | 3/2002 |
| WO | WO 02/26080 A1 | | 4/2002 |
| WO | WO 02/28221 A1 | | 4/2002 |
| WO | WO 03/15574 A1 | | 2/2003 |
| WO | WO 03/015575 A1 | | 2/2003 |
| WO | WO 03/020076 A1 | | 3/2003 |
| WO | WO 2004/028293 A1 | | 4/2004 |
| WO | WO 2004/028398 A1 | | 4/2004 |

* cited by examiner

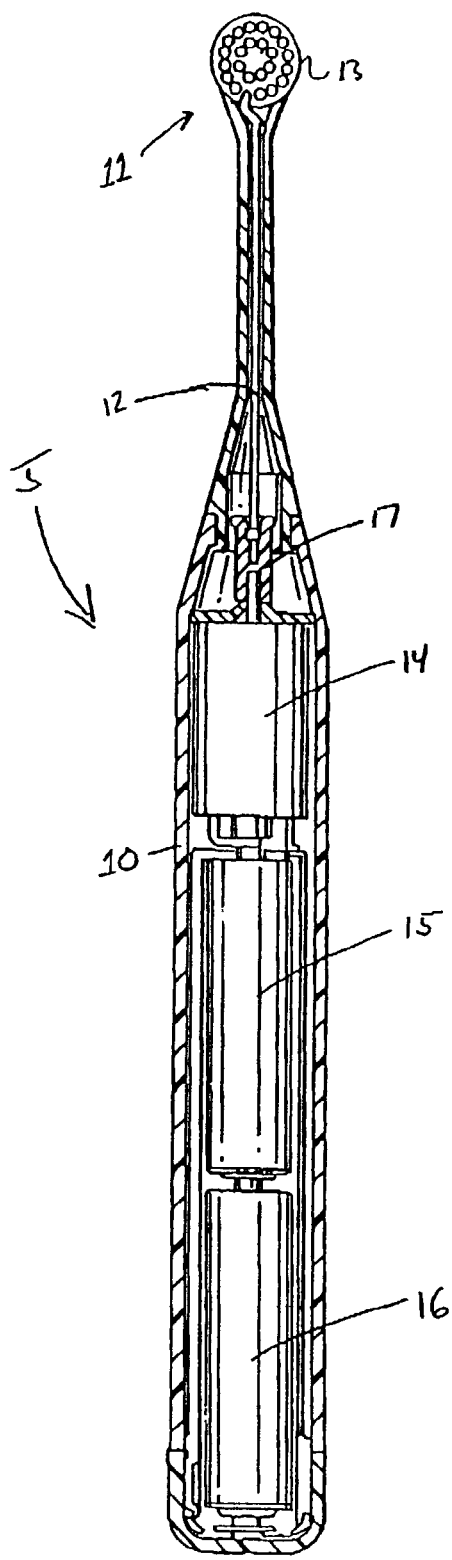
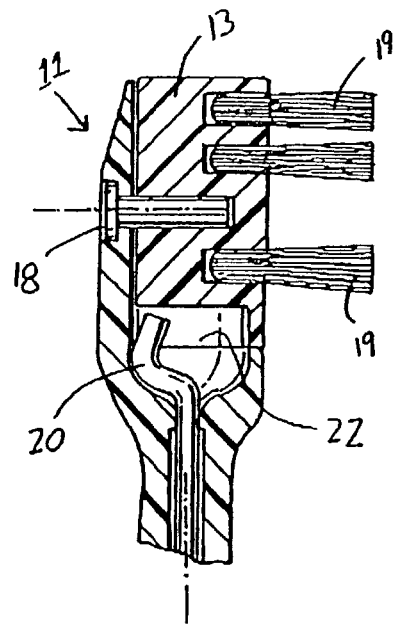
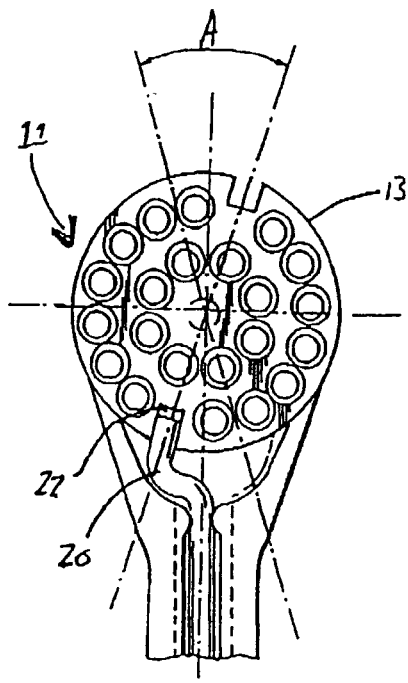
FIG. 1A (PRIOR ART)
FIG. 1B (PRIOR ART)
FIG. 1C (PRIOR ART)

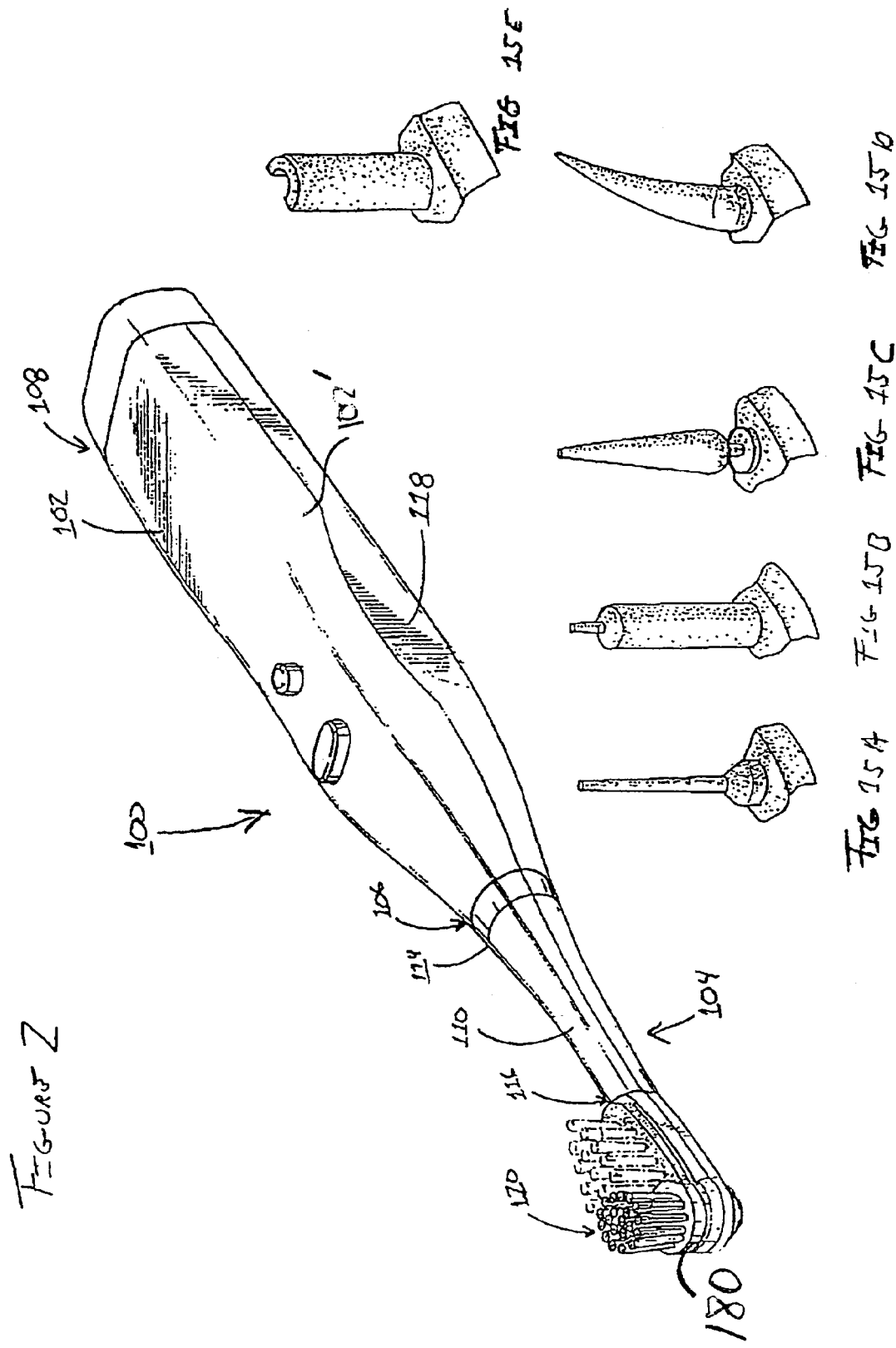

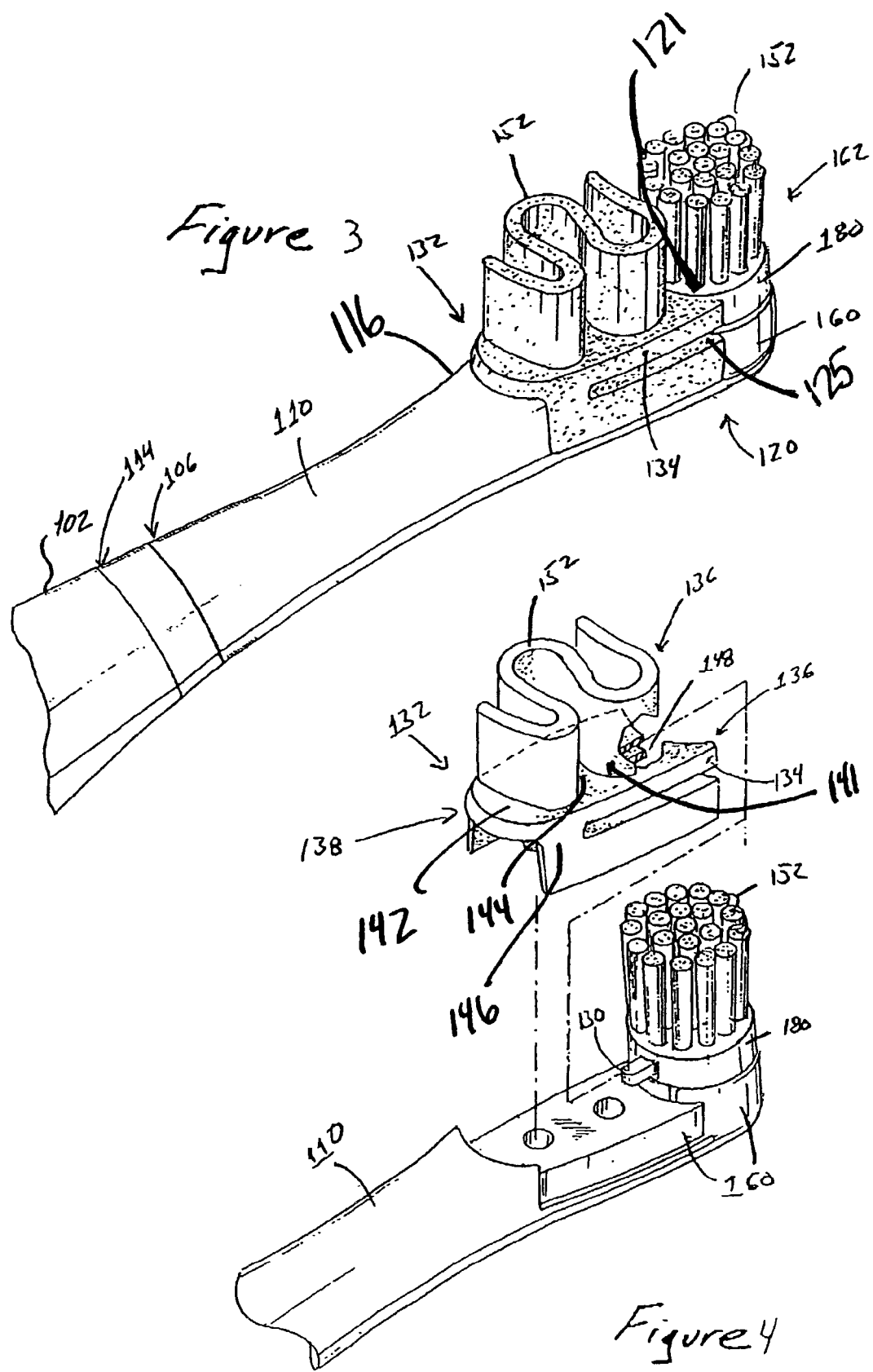

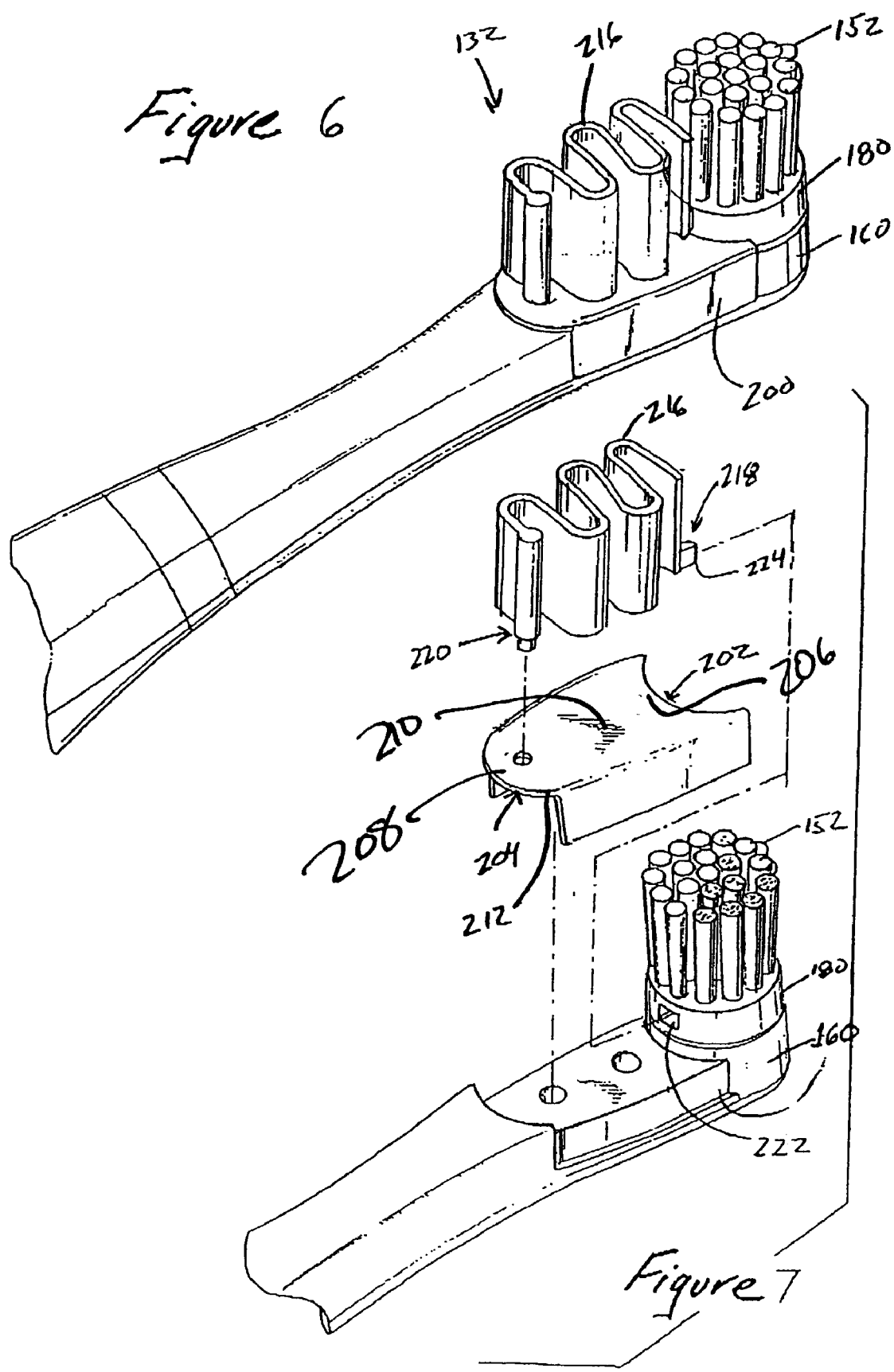

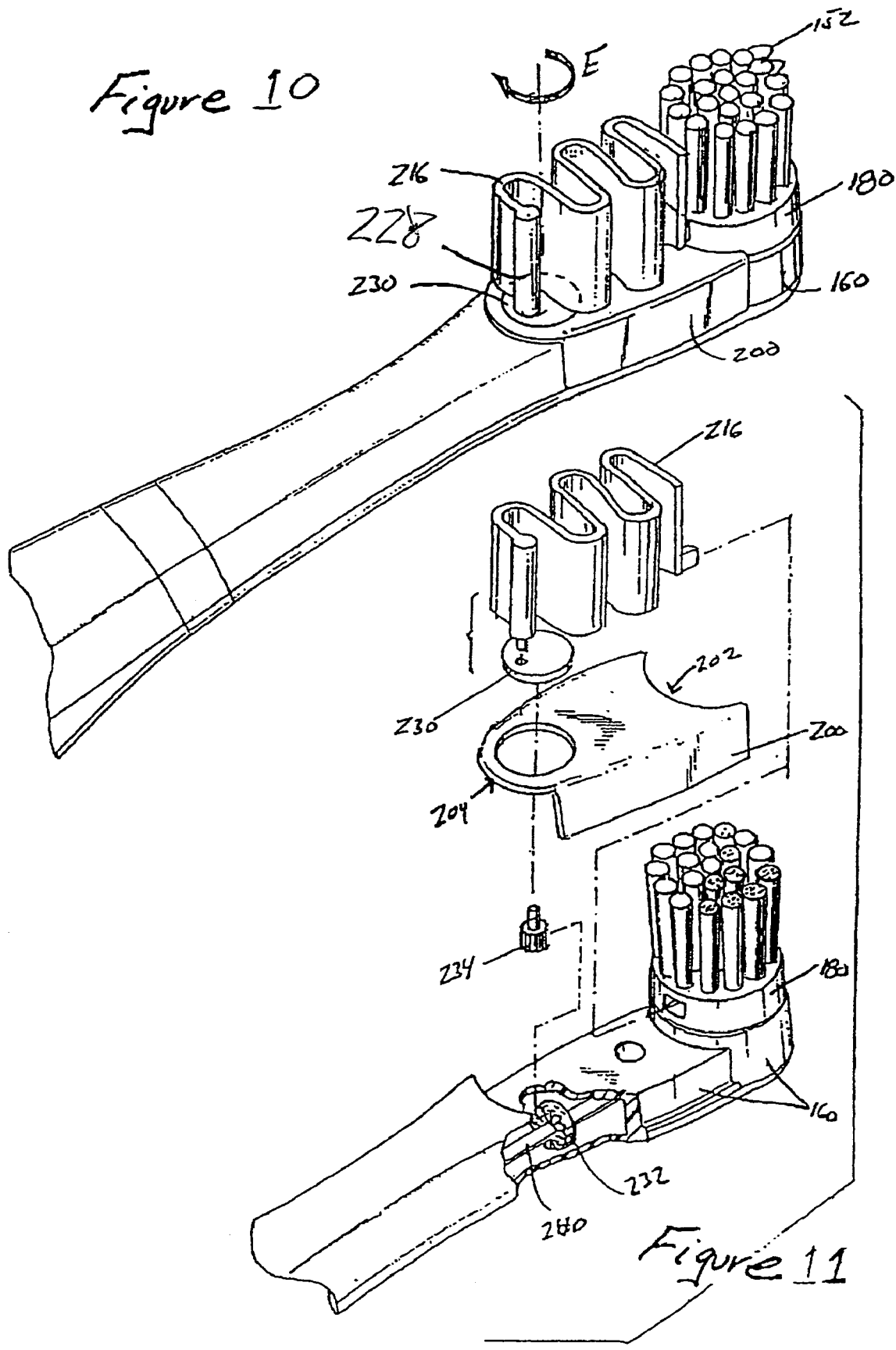

POWER TOOTHBRUSH AND POWER SOURCE

BACKGROUND OF THE INVENTION

1. Field of the Invention

The present invention relates to powered toothbrushes, and more particularly, to a toothbrush having a head with two distinct moving sections that each provide oral health benefits to the user.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of toothbrush by the user, provide superior cleaning than manual toothbrushes. Typically, powered toothbrushes are powered by disposable or rechargeable batteries that power an electric motor that in turn drives toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw, and each row of teeth consequently has a convex outer curve and a concave inner curve. Individual teeth often have extremely complex surfaces, with areas that may be flat, concave, or convex. The more precise conformation between the bristles and the tooth surface, the more effective toothbrush may be in cleaning, whitening and/or stimulating.

Known powered toothbrushes typically arrange the bristles in a compact conical or cylindrical pattern on a generally circular, disk-shaped bristle carrier. The powered toothbrush heads are traditionally compact, generally oval in shape and heads are produced with a flat trimmed bristle pattern. Alternatively, other head shapes and bristle patterns are available.

One example of a powered toothbrush is depicted in U.S. Pat. No. 5,625,916 to McDougall, which is hereby incorporated by reference in its entirety. Toothbrush shown in McDougall has a disc-shaped bristle carrier. The bristle carrier, and thus the bristles, are driven in a vibrating or oscillating manner. This type of toothbrush is described herein with reference to FIGS. 1A–1C. A toothbrush 5 includes a handle portion 10 at a proximal end of toothbrush 5 and a head 11 at a distal end of toothbrush 5. Handle portion 10 has compartments for containing a powered motor 14 and batteries 15 and 16. Head 11 includes a generally circular bristle holder (carrier) 13. A rotatable shaft 12 extends from the motor 14 to head 11. A shaft coupling 17 may be located along the shaft 12 and configured to provide for the shaft 12 to be separated at a point between the motor 14 and head 11. This permits the shaft to be removed from toothbrush 5, e.g., for cleaning, servicing, or replacement.

Head 11 includes a post 18 that provides a rotational pivot axis for the bristle holder 13 containing bristle tufts 19. The distal end of the shaft 12 has a journal or offset 20 that is radially displaced from the longitudinal axis of the shaft 12, which may be integrally formed therewith. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Although powered toothbrushes such as those described immediately above provide advantages over manual toothbrushes, they are subject to various limitations. Providing a rotating or oscillating bristle holder (carrier) with a typical oblong or oval toothbrush head constrains the size of the moving bristle holder, and consequently the area of bristles available for teeth cleaning. Also, when the bristles are placed in contact with the teeth during brushing, there is less bristle contact with adjacent areas, such as the gums. Thus, while these compact bristle patterns provide for cleaning, there is minimal whitening and stimulation.

One attempt to overcome the limitations associated with a small powered bristle area is shown in U.S. Pat. No. 6,000,083 to Blaustein et al. toothbrush in Blaustein et al. has a bristle area and pattern similar to a manual toothbrush, but an area of the bristles has simply been replaced by a powered bristle section. The result is that head has a powered or moving bristle section and static bristle section. The limitation of Blaustein et al. is that the static bristle section provides no better cleaning, whitening or stimulation than a manual toothbrush.

International Application No. PCT/EPO1/07615 of Braun GmbH discloses a powered toothbrush with two separate bristle parts that can move. Each bristle part can have a different range and/or type of motion. However, only one bristle part is powered. The other unpowered bristle part moves due to a resonance effect imparted by the frequency of the movement of the first bristle part.

This free resonance causes a number of difficulties. First, because any contact between the bristle parts will dampen or cancel any resonance of the unpowered bristle part, the unpowered bristle part "floats" separately from the powered bristle part. This necessitates separation or gaps between them. These gaps expose the internal workings of the head to foreign matter such as water, saliva, toothpaste, and food particles. This foreign matter may interfere with the workings of the unpowered bristle head. For example, the unpowered bristle part is spring-loaded to assist its resonance. Foreign matter may accumulate on or around the spring, interfering with its function. In addition, food particles may remain in the head and may fester and host microorganisms, which are undesirable if not potentially harmful when introduced directly into the mouth.

Another limitation of such a design is that movement of the unpowered bristle part may be damped by contact with the teeth, or lessened when the frequency of the powered part shifts from the resonance frequency. This can occur due to pressure imparted against the powered bristle part by the teeth or gums during brushing. Finally, the energy imparted to the unpowered bristle part is only a portion of the energy input into the powered part. Therefore, the unpowered bristle part is less effective in cleaning than the powered part, limiting the overall effectiveness of toothbrush.

Thus, there is a need in the art for a powered toothbrush with increased effectiveness through a larger area of powered or driven bristles or bristles that are otherwise movable. There is also a need for a toothbrush having increased whitening and/or stimulation than known toothbrushes. There is further a need for such improved toothbrushes to be comparable in manufacturing and purchasing costs as known powered toothbrushes.

SUMMARY OF THE INVENTION

A powered toothbrush is provided and includes a handle portion at a proximal end and either a fixed head or a linkage for receiving a removable head at a distal end thereof. A neck is further formed between the handle portion and the head. According to one embodiment of the invention, the head includes two distinct movable parts that each and together provide oral health benefits, each being adapted to have a number of bristles or elastomeric cleaning members extending therefrom adapted to contact surfaces of one or more teeth and surrounding areas. The powered toothbrush is further formed with a drive mechanism that imparts movement to the first movable part to deliver a cleaning, polishing, whitening action that supplements the cleaning efficiency of a typical powered toothbrush. The first movable part in turn imparts movement to the second movable part.

In one embodiment, the first movable head part is a first bristle carrier that supports a number of bristle tufts, elastomeric cleaning members, or a combination thereof. The first bristle carrier is operatively mounted to the head and is coupled to the drive mechanism such that the first bristle carrier oscillates back and forth in a direction parallel to the toothbrush head. Preferably, the oscillating first bristle carrier is moved back and forth in a rotational direction. The second movable part is in the form of a second carrier that is coupled to the head and includes an upstanding elastomeric element disposed along an upper surface thereof. The elastomeric element has a first end that is coupled to the head and a second end that engages the first carrier so that the movement of the first carrier in the first direction is translated into movement of the elastomeric element in a second direction.

Additionally, a single battery may be employed rather than the conventional two battery system. The use of one battery allows for modification of the structure of the handle to be more user friendly. Furthermore, use of a single battery may ease battery changes and prolong the life of the power system.

Other features and advantages of the present invention will be apparent from the foregoing detailed description when read in conjunction with the accompanying drawings.

The invention accordingly comprises the several steps and the relation of one or more of such steps with respect to each of the others, and the apparatus embodying features of construction, combination(s) of elements and arrangement of parts that are adapted to effect such steps, all as exemplified in the following detailed disclosure, and the scope of the invention will be indicated in the claims.

BRIEF DESCRIPTION OF THE DRAWING FIGURES

For a more complete understanding of the invention, reference is made to the following description and accompanying drawings, in which:

FIG. 1A is a front partial cross-sectional view of a conventional powered toothbrush including a head;

FIG. 1B is a partial side cross-sectional view of the toothbrush head of FIG. 1A;

FIG. 1C is a partial front cross-sectional view of the toothbrush head of FIG. 1A;

FIG. 2 is a front and side perspective view of a powered toothbrush according to one exemplary embodiment of the invention showing a toothbrush head having distinct first and second movable sections constructed in accordance with the invention;

FIG. 4 is a front and side perspective exploded view of the powered toothbrush head of the powered toothbrush of FIG. 3;

FIGS. 5A–5C are front views of the powered toothbrush head of FIG. 3 in various positions generated when in motion;

FIG. 6 is a front and side perspective view of another embodiment of a powered toothbrush head of the powered toothbrush of FIG. 2;

FIG. 7 is a front and side perspective exploded view of the powered toothbrush head of the powered toothbrush of FIG. 6;

FIG. 10 is a front and side perspective view of another embodiment of the powered toothbrush head of the powered toothbrush of FIG. 2;

FIG. 11 is a front and side perspective exploded cut-away view of the powered toothbrush head of the powered toothbrush of FIG. 10;

FIG. 15A is a perspective view of an elastomeric tooth care element having a first configuration and adapted for use in a toothbrush head constructed in accordance with the invention;

FIG. 15B is a perspective view of an elastomeric tooth care element having a second configuration and adapted for use in a toothbrush head constructed in accordance with the invention;

FIG. 15C is a perspective view of an elastomeric tooth care element having a third configuration and adapted for use in a toothbrush head constructed in accordance with the invention;

FIG. 15D is a perspective view of an elastomeric tooth care element having a fourth configuration and adapted for use in a toothbrush head constructed in accordance with the invention; and FIG. 15E is a perspective view of an elastomeric tooth care element having a fifth configuration and adapted for use in a toothbrush head constructed in accordance with the invention.

DETAILED DESCRIPTION OF CERTAIN PREFERRED EMBODIMENTS OF THE PRESENT INVENTION

Figure 3C:
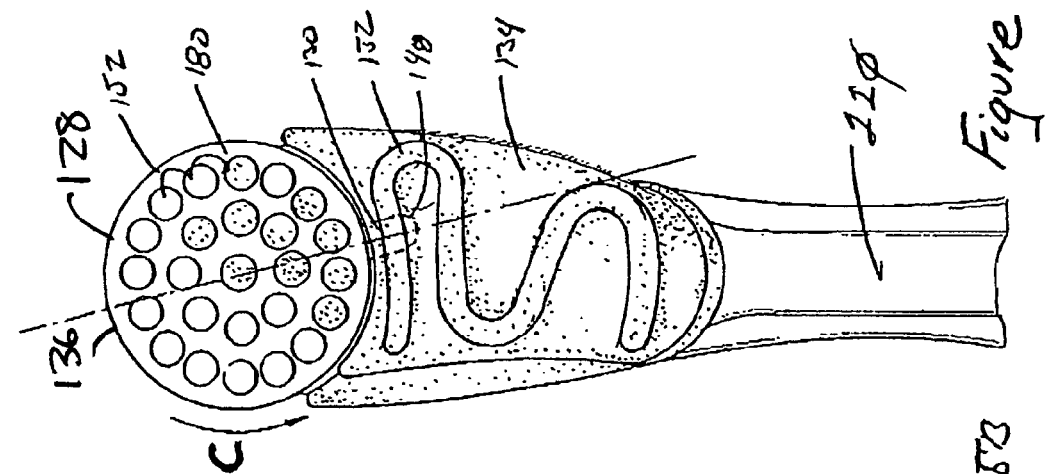
FIG. 3 is a front and side perspective view of the powered toothbrush head according to another exemplary embodiment of a powered toothbrush constructed in accordance with the invention.

Referring first to FIG. 2, an exemplary powered toothbrush according to a first embodiment of the invention is illustrated and generally indicated at 100. Toothbrush 100 includes a handle 102 at a proximal end thereof that defines an interior compartment (not illustrated) for housing various toothbrush components, and a brush section 104 that is defined by a neck 110 that terminates in a head 120 at a distal end of toothbrush 100.

The interior compartment of the handle typically houses, in addition to other components, a power source. This power source typically comprises two standard size batteries. Thus, the size and shape of the handle is limited by the required power.

In accordance with the invention, a single battery may be tightly fit into a battery compartment housing 102' of the handle 102 purposefully designed to receive the battery. The single battery preferably is formed with a diameter of a range between approximately 10.5 mm to 14.5 mm. However, it is envisioned that the diameter may be of a range between 8.3 mm and 34.2 mm. By using a single battery instead of multiple batteries, a smaller compartment for the battery may be utilized thus reducing the size of the powered toothbrush. This allows for greater freedom in designing a more user friendly handle, and insuring that all available power is used.

Handle 102 has a free proximal end 108 and an opposite neck end 106. Neck 110 generally includes a first end 114 and a second end 116 with first end 114 being located at neck end 106 of handle 102 and the second end 116 being located at head 120. In other words, neck 110 is the portion of toothbrush 100 that extends between handle 102 and head 120. Neck 110 also defines an interior compartment (not shown) for housing various working components of toothbrush 100. Head 120 is preferably generally aligned with the longitudinal axis of toothbrush 100.

Neck 110 and handle 102 may be constructed as a unitary member by forming neck 110 integral to handle 102 at neck end 106 of handle 102, or may be formed detachable from handle 102 at neck end 106 of neck 110. In accordance with this detachable embodiment, the combined neck 110 and head 120 can be removed from handle 102 to permit cleaning, servicing and/or interchanging of either handle 102 or the combined neck 110 and head 120 (brush section 104). When neck 110 is formed to be detachable from handle 102, first neck end 114 preferably includes a connector linkage (not illustrated) that is adapted to be detachably joined to handle 102 using traditional techniques. It will also be appreciated that the point of detachment may be between head 120 and neck 110 such that head 120 is of a refill head type. Furthermore, head 120 is formed of a first bristle carrier 180 and a second bristle carrier 132.

It will further be appreciated that the illustrated shapes of handle 102 and neck 110 are merely exemplary in nature and handle 102 and/or neck 110 can be formed to have any number of shapes. Preferably, the shapes of handle 102 and neck 110 are ergonomically pleasing to a user of toothbrush 100 and provide a toothbrush that is easily gripped and held and easily manipulated by the user. For example, handle 102 may include slightly recessed finger sections 118 which are formed on opposite sides of handle 102. One recessed finger section 118 is designed to receive the thumb of one hand and the other recessed finger section 118 is designed to receive one or more other fingers of the same hand to thereby assist the user in proper placement of toothbrush 100 in the user's hand. One or more of recessed finger sections 118 may include ribs or another type of roughened surface to assist the user in gripping toothbrush 100 at recessed finger sections 118.

Figure 3B:
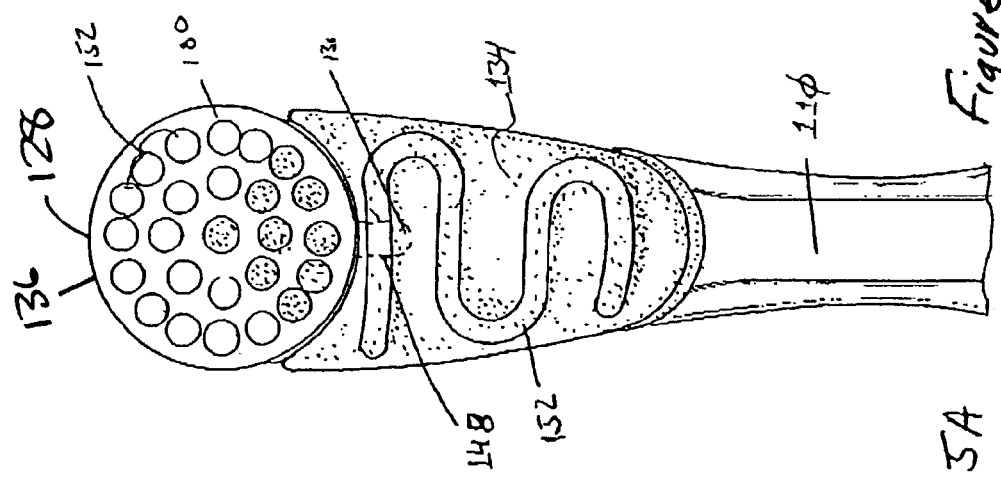
Figure 3A:
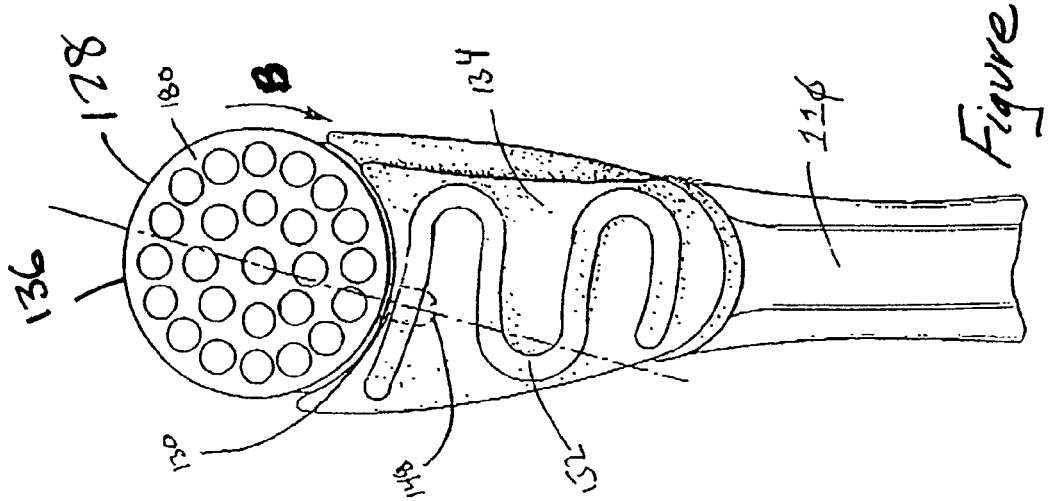

Referring next to FIGS. 3 and 4, an additional embodiment of a powered toothbrush head is shown. A head 120 of toothbrush 100 includes a head base 160 that partially defines an inner compartment 125 of head 120. Head base 160 may be constructed so that it terminates in a rounded distal end 162, which also defines the distal end of toothbrush 100. Preferably, head base 160 is integrally attached to second end 116 of neck 110.

Head 120 also includes a first movable bristle carrier 180 which is illustrated as being at the outermost or distal portion of head 120. First bristle carrier 180 may have a construction that is either identical to or similar to that of the bristle holders 13 or 121 illustrated in FIGS. 1A–1C and FIG. 2. First movable bristle carrier 180 is preferably formed with a disk having circular cross-section since it is intended to oscillate in a rotational manner about a center point thereof. First movable bristle carrier 180 is formed with a protrusion 130 directed toward a second movable bristle carrier 132. However, it will be appreciated that first movable bristle carrier 180 is not limited to having a disk shape and can have any number of different shapes, such as an oval or various other regular or irregular shapes, so long as first moveable bristle carrier 180 is able to oscillate in a substantially rotational manner. A circular shape is preferred since it requires the least amount of clearance to accommodate the oscillating movement.

A plurality of tooth care elements 152 are coupled to and extend outwardly from first movable bristle carrier 180 in a direction substantially perpendicular to a plane defined by a face of first movable bristle carrier 180. As used herein, the term "tooth care elements" includes any type of structure that is commonly used or is suitable for use in providing oral health benefits (e.g., tooth cleaning, tooth polishing, tooth whitening, etc.) by making intimate contact with surfaces of the teeth and surrounding areas. Such tooth care elements include but are not limited to tufts of bristles that can be formed to have a number of different shapes and sizes, and various elastomeric members (see FIGS. 15A–15E) that can be formed to have a number of different shapes and sizes, or a combination of both. Bristle tufts arranged on first bristle carrier 180 is only one exemplary configuration and it will be understood that other bristle configurations (such as stapled, IMT, etc.) can be used. Bristle tufts may all be formed of the same or different bristle materials (such as nylon bristles, spiral bristles, rubber bristles, etc.) Moreover, while the tooth care elements can be arranged so that they are generally perpendicular to the face of first bristle carrier 180 (as noted above), some or all of the tooth care elements can be angled at various angles with respect to first bristle carrier 180 as desired. When first bristle carrier 180 includes bristle tufts, it is thereby possible to select the combination of bristles configurations, bristle lengths, bristle materials and bristle orientations to achieve specific intended results, such as to create as much movement from the moving tuft heads to deliver additional oral health benefits such as enhanced cleaning, tooth polishing and/or tooth whitening.

While first bristle carrier 180 has been defined as a movable bristle carrier 180, it will be understood that first movable carrier 180 is not limited to having only tufts of bristles as a part thereof. Instead, first movable carrier 180 is to be broadly considered as being a carrier for any number of suitable tooth care elements 152 or any number of combinations of different types of tooth care elements 152. For example, first movable carrier 180 may include a number of elastomeric members to provide the desired oral health benefits. The elastomeric members may be attached to first movable carrier 180 using conventional techniques, including integrally forming the elastomeric members with an upper surface of carrier 180. Tooth care elements 152 provided as part of first movable carrier 180 can thus be entirely of one type (e.g., bristle tufts or elastomeric members) or can be formed according to a mixed arrangement.

FIGS. 15A–15E illustrate various exemplary elastomeric members that serve as tooth care elements 152. FIG. 15A shows an elastomeric tooth care element in the form of a thin spike; FIG. 15B shows an elastomeric tooth care element in the form of a barrel spike; FIG. 15C shows an elastomeric tooth care element in the form of a squeegee point; FIG. 15D shows an elastomeric tooth care element in the form of an angled point; and FIG. 15E shows an elastomeric tooth care element in the form of a section of an elastomeric wall. The elastomeric wall of FIG. 15E can have a linear, planar shape; a zigzag shape; a serpentine shape, etc. All of the above elastomeric tooth care elements can have smooth textures or can have rough surfaces. In addition, the wall sections of the elastomeric tooth care elements can be vertically straight, taper toward inward toward one end or expand toward one end. The tops of the elastomeric tooth care walls can have a planar surface or can have a protrusion (i.e., hump) or the like formed thereat.

For purpose of illustration only, first movable carrier 180 will be described as containing a predetermined number of bristle tufts; however the following features apply equally to the situation where first movable carrier 180 is formed entirely or partly of elastomeric members. The bristle tufts of first movable carrier 180 may be formed with uniform heights or non-uniform heights. For example, first movable carrier 180 may include bristle tufts having a first height as well as bristle tufts having a second different height.

First movable bristle carrier 180 is constructed so as to pivotally rotate about a center point thereof, thereby effectuating movement of the bristle tufts and/or elastomeric members that extend outwardly from first movable bristle carrier 180. The movement of first movable bristle carrier 180 is preferably an oscillation type movement as first movable bristle carrier 180 pivots about a post at a center point thereof (see FIG. 1). First movable bristle carrier 180 is formed with a slot or opening (not illustrated). This slot is preferably identical to or substantially similar to slot 22 illustrated in FIGS. 1A–1C. Preferably, slot 22 is formed at a peripheral edge of first movable bristle carrier 180 and extends along a substantial height of first movable bristle carrier 180. For example, slot 22 preferably does not extend to the upper surface of first bristle carrier 180 where the tooth care elements are positioned. Instead, slot 22 preferably has a closed upper end to prevent foreign matter, such as saliva, toothpaste, foreign particles, etc., from entering slot when the operator is performing a brushing operation. The opposite end of slot 22 that is located within the inner compartment 125 of head 140 can be open.

Toothbrush 100 includes a drive mechanism to effectuate movement of certain parts of the toothbrush, and more specifically, for causing movement of first movable bristle carrier 180. One exemplary drive mechanism is disclosed in U.S. Pat. No. 5,625,916 to McDougall, which has been previously incorporated herein by reference and includes a rotating drive shaft 240 that extends at least through neck 110 (i.e., the inner compartment thereof). Drive shaft 240 preferably has a construction that is the same as or similar in nature to shaft 12 illustrated in FIGS. 1A–1C.

Drive shaft 240 has one end (not illustrated) that is operatively connected to a drive member (not illustrated), such as a motor or any other type of drive device, for imparting movement to first movable bristle carrier 180. Drive shaft 240 is formed with an opposing distal end (not illustrated) that is bent such that the end is not axially aligned with the longitudinal axis of drive shaft 240. This distal end may be formed similar to the end 20 of FIGS. 1A–1C or may be formed differently so long as it performs the intended function. In other words, the end is an offset crank end of drive shaft 240 and is configured to be received in slot 22 so that a 360° rotational movement of shaft 240 is transmitted into an oscillating back and forth rotational movement of first movable bristle carrier 180.

The drive mechanism for powered toothbrush 100 can be any type of drive, e.g. a rotating drive, an oscillating drive, an eccentric drive, an unbalanced-generated drive, a drive having one more gearing mechanisms, and/or the like, that is capable of performing the intended function. The drive mechanism can be realized in the form of an electric motor or other type of motor and the movement generated by the drive can be imparted to one or more sections of the head 120 or to other elements that can be present in the brush section, such as bristle tufts, elastomeric members. The movement can be imparted directly though a driving axle, such as drive shaft 240 or it can be imparted through a driving post attached to the driving axle. When toothbrush 100 includes an oscillating drive mechanism either identical or similar to the exemplary drive mechanism illustrated in FIGS. 1A through 1C, the interior compartment of handle 102 houses a motor operatively connected to drive shaft 240 and a source to power the motor, such as one or more batteries.

When the drive mechanism is actuated and drive shaft 240 is rotated, the movement of the crank end thereof imparts an oscillating back and forth movement of first movable bristle carrier 180 through an angle between about 10° to about 120° and in a preferred exemplary embodiment, the movement is through an angle between about 10° to about 30°, and in a most preferred embodiment is through an angle between about 10° to about 15°.

The toothbrush 100 further includes a second movable bristle carrier 132 that is operatively mounted on the head 120. The second movable bristle carrier 132 comprises a platform 134 having a first end 136, a second end 138, a first midpoint 141, a second midpoint 142, a midpoint 144, and a bottom 146. The platform 134 defines a recess 148 that is preferably defined at the first end 136 and protrusion 130 of first movable bristle carrier 180 is received into recess 148. The movement of first movable bristle carrier 180 directly imparts movement to platform 134.

There are numerous portions of the present invention, that when changed in accordance with various embodiments of the invention, will change the type and range of motion of both first movable bristle carrier 180 and second movable bristle carrier 132. The movement of first movable bristle carrier 180 is outlined above and can be altered by varying the drive or transmission of the motion of that drive to first movable bristle carrier 180. These variations are well known in the art.

However, changes in second movable bristle carrier 132 can vary its movement as well. Various embodiments may be designed so that protrusion 130 of the first movable bristle carrier 180 is rigidly received in the recess 148, or protrusion 130 may be frictionally received in recess 148.

In the preferred embodiment, tooth care element 152 is an elastomeric tooth care element formed of an elastomeric wall and it can have a linear, planar, zigzag or serpentine shape. Tooth care element 152 may travel from second end 138 to first end 136 of the platform 134.

FIGS. 5A–5C illustrate another exemplary embodiment in which second movable bristle carrier 132 is attached to platform 134 and head base 160. FIGS. 5A–5C illustrate first end 136 of first movable bristle carrier 180 oscillating in a clockwise motion B and counterclockwise motion C, respectively. The clockwise motion B and counterclockwise motion C forces protrusion 130 to engage recess 148 and cause platform 134 to move in a direction both parallel and perpendicular to first end 136. This clockwise motion B and counterclockwise motions C also force tooth care element 152 to stretch or compress. FIG. 5B illustrates first movable bristle carrier 180 and platform 134 at rest.

Referring next to FIGS. 6 through 9, another exemplary head embodiment is illustrated. The handle 102, neck 110, drive, and head base 160 may be the same as described above. However, first movable bristle carrier 180 defines one or more recesses 222 directed toward second movable bristle carrier 132. Second movable bristle carrier 132 includes a carrier base 200 having a first end 202, a second end 204, a first end midpoint 206, second end midpoint 208, a midpoint 210, and a bottom 212. Additionally, a continuous elastomeric polishing element 216 is formed with a carrier end 218 and a far end 220. Continuous elastomeric polishing element 216 is attached to first movable bristle carrier 180 at carrier end 218 via a protrusion 224 engaging recess 222, and is attached to carrier base 200 at far end 220. In the displayed embodiment, far end 220 passes through a hole in base 204, and directly engages base 160. The movement of first movable bristle carrier 180 directly imparts movement to continuous elastomeric polishing element 216 via the interaction of recess 222 and protrusion 224.

Continuous elastomeric polishing element 216 may include a plurality of elastomeric contact elements linked continuously together. In a preferred embodiment, the continuous elastomeric polishing element 216 is formed as a wall. Regardless of the elastomeric contact elements that comprise the continuous elastomeric polishing element 216, the continuous elastomeric polishing element 216 may traverse certain fixed paths. The continuous elastomeric polishing element 216 may traverse a straight path, zigzag path or a serpentine path between the carrier end 218 and the fixed end 220.

Figures 8A, 8B:
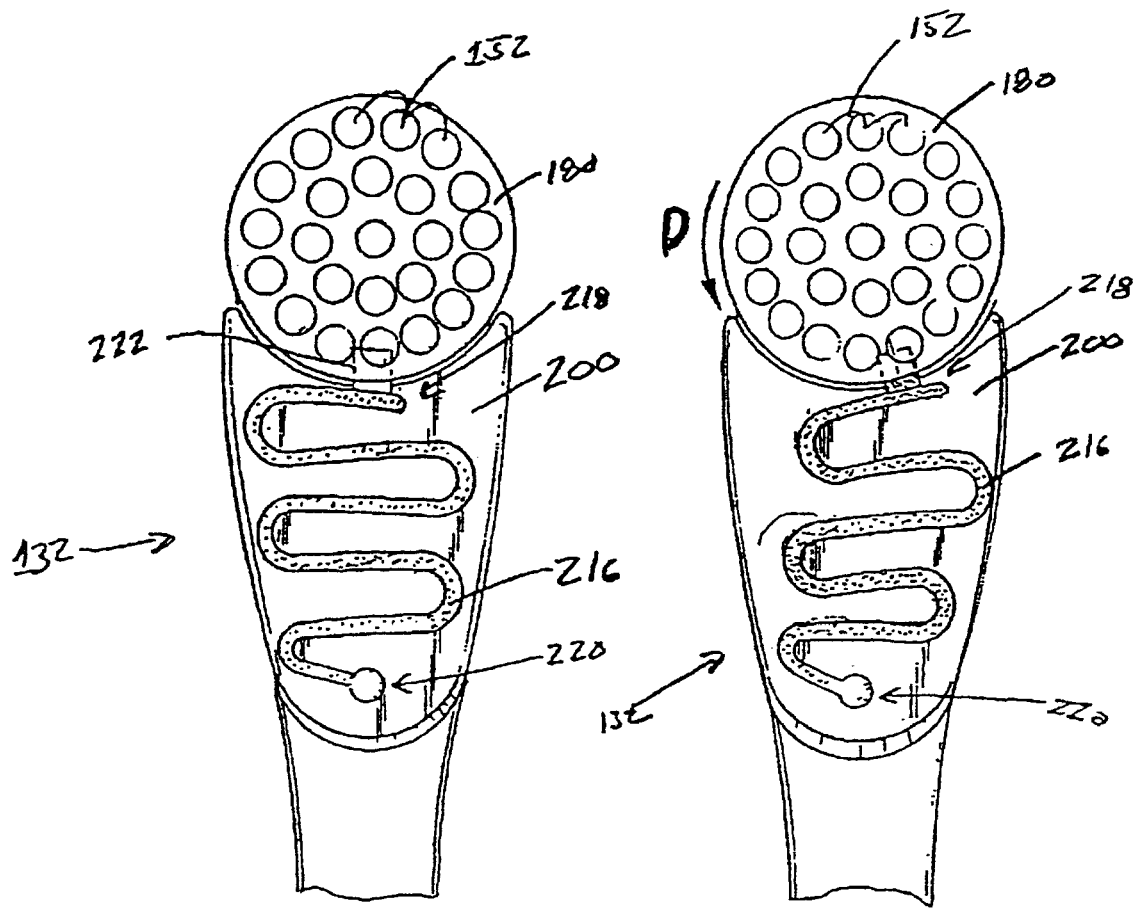
FIGS. 8A–8B are front views of the powered toothbrush head of FIG. 6 in various positions generated when in motion.

FIGS. 8A and 8B illustrate the second preferred embodiment in motion. FIG. 8A illustrates first movable bristle carrier 180 at rest. FIG. 8B illustrates first movable bristle carrier 180 oscillating in a counterclockwise motion D. The counterclockwise motion D of first movable bristle carrier 180 causes the continuous elastomeric polishing element 216 to elongate and translate in a direction parallel to the movement of carrier end 218. Thus, while motion has been shown in the counterclockwise direction, it will be understood that first movable bristle carrier 180 can oscillate in the clockwise direction, thus compressing the continuous elastomeric polishing element 216 as well as translating it in a direction parallel to the movement of carrier end 218. It is also illustrated, as noted above, that the continuous elastomeric polishing element 216 is attached to the first movable bristle carrier 180 by way of protrusion 224 entering recess 222. It will be well understood that the continuous elastomeric polishing element 216 can be connected to the first movable bristle carrier 180 in numerous ways known in the art.

Figure 9:
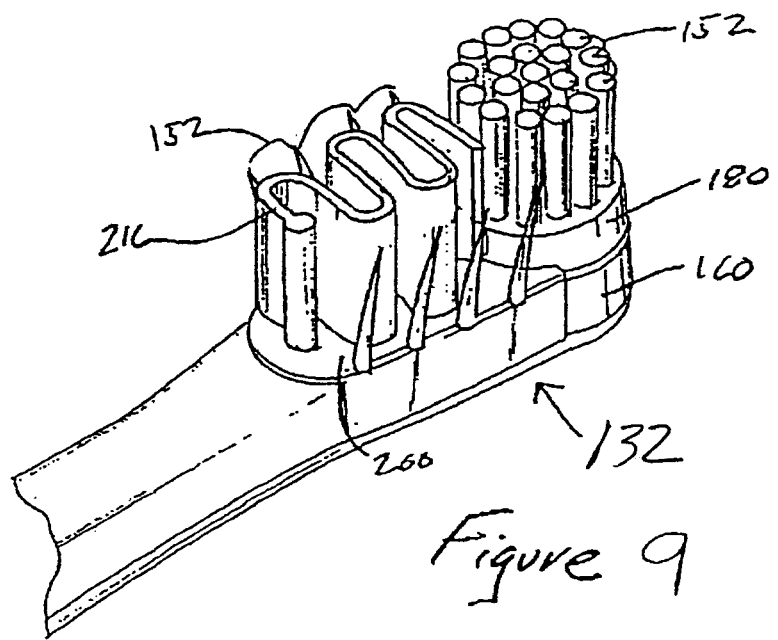
FIG. 9 is a front and side perspective view of another embodiment of the powered toothbrush head of the powered toothbrush of FIG. 2.

Referring additionally to FIG. 9, second movable bristle carrier 132 may further include a plurality of tooth contact elements 152 attached to carrier base 200.

Referring next to FIGS. 10 through 14, another exemplary embodiment constructed in accordance with the invention is shown. This embodiment is similar to the previous embodiment with the exception that this embodiment contains an additional feature. The powered toothbrush now includes a third movable bristle carrier 230 drivingly engaged to the drive mechanism to enable movement of third tooth contact element carrier 228. Continuous elastomeric polishing element 216 is attached to third movable bristle carrier 230 at far end of the continuous elastomeric polishing element 216. Third movable bristle carrier 230 is preferably formed as a disk of circular cross-section since it is intended to oscillate in a rotational manner. However, it will be appreciated that the third movable bristle carrier 230 is not limited to having a disk shape and can have any number of different shapes, such as an oval or various other regular or irregular shapes, so long as the third movable bristle carrier 230 can oscillate in a rotational manner, vibrate, translate or move in a combination thereof. A circular shape is preferred since it requires the least amount of clearance to accommodate the oscillating movement. The rotational movement of third movable bristle carrier 230 may include rotation through an angle of about 360° (arrow E). The vibrational movement of the third movable bristle carrier 230 can include vibration perpendicular to the axis of head 120. The translation movement may be a translation from about first movable bristle carrier 180 to about second end 204 of carrier base 200. The lateral movement of the third movable bristle carrier 230 may be a movement parallel to second end 204 of carrier base 200.

As with the other embodiments, continuous elastomeric polishing element 216 may traverse certain fixed paths in this embodiment. Continuous elastomeric polishing element 216 may traverse a straight path, zigzag path or a serpentine path between carrier end 218 and fixed end 220.

FIG. 11 illustrates a sample gearing system to drive third movable bristle carrier 230. A main gear 232 is fixed to drive shaft 240 and meshingly engaged to a minor gear 234. Minor gear 234 is operatively connected to third movable bristle carrier 230 and imparts a driving movement from drive shaft 240 thereto. However, it will be appreciated that third movable bristle carrier 230 is not limited to the gearing system illustrated above, third movable bristle carrier 230 can be driven from a drive shaft 240 any number of ways so long as the third movable bristle carrier 230 is driven.

Figure 12:
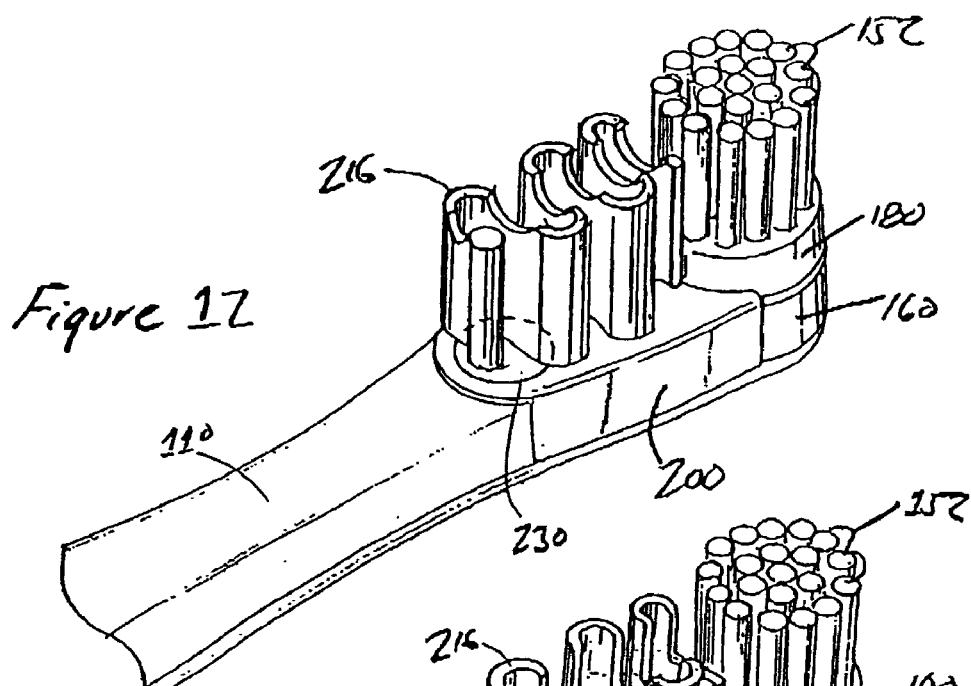
FIG. 12 is a front and side perspective view of another embodiment of the powered toothbrush head of the powered toothbrush of FIG. 2.
Figure 13:
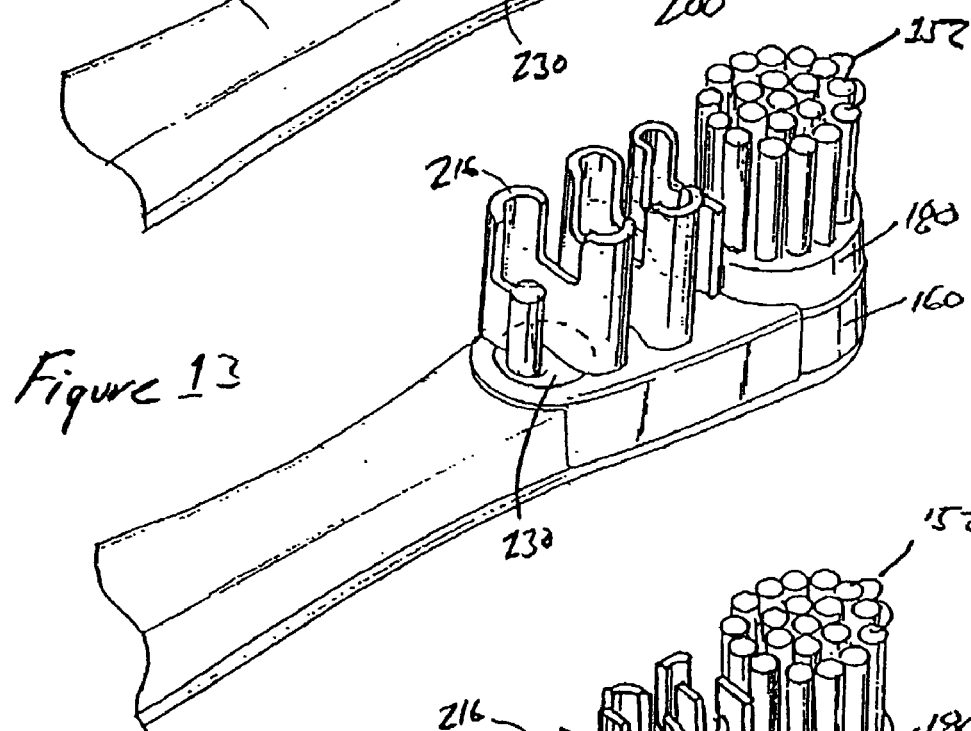
FIG. 13 is a front and side perspective view of another embodiment of the powered toothbrush head of the powered toothbrush of FIG. 2.
Figure 14:
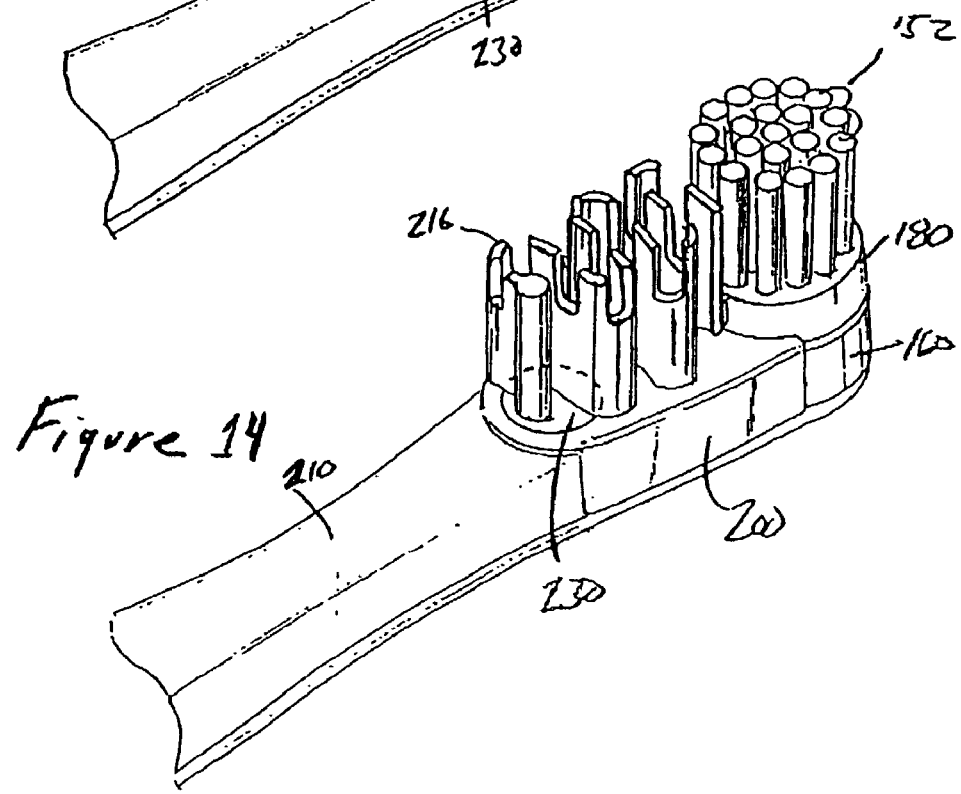
FIG. 14 is a front and side perspective view of another embodiment of the powered toothbrush head of the powered toothbrush of FIG. 2.

FIGS. 12 through 14 illustrate additional exemplary embodiments of continuous elastomeric polishing element 216. The continuous elastomeric polishing element 216 may have a hump, a large set of projections or a smaller set of projections.

A powered toothbrush made in accordance with any of the present embodiments offers a number of advantages over conventional powered toothbrushes that are presently available. First movable bristle carrier 180 oscillates back and forth, or moves otherwise. As the operator brushes his or her teeth, the oscillating tooth care elements (i.e., bristle tufts and/or elastomeric members) contact the surfaces of the teeth and the surrounding areas to deliver enhanced cleaning, tooth polishing and/or tooth whitening. The elastomeric second bristle carrier 132 permits a number of additional tooth care elements to be disposed in a number of different patterns. The increased number of moving tooth care elements of second bristle carrier provides increased contact with gingival tissues and enhanced massaging thereof.

The toothbrush according to the various embodiments disclosed herein can be made from any number of materials that are suitable for use in oral care products, such as toothbrushes, etc. For example, many of the components that are included in toothbrush are formed of plastic materials. Accordingly, the handle and head of the powered toothbrush may be molded from polyolefins such as polypropylenes and polyethylenes, polyamids such as nylons, and polyesters such as polyethylene terephthalate. Other suitable materials include polymethylmethacrylate, styrene acroylonitrate and cellulose esters, for example cellulose propionate.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyamide 6), polyesters (for example polyester ester or polyether ester), polyurethanes (for, example polyesterurethane, polyetherurethane or polyesteretherurethane).

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A powered toothbrush comprising:
   a handle portion being formed with a neck at one end thereof, the handle portion being adapted to receive a battery in an interior compartment defined therein; and
   a head coupled to the neck, the head further including:
      a base; and
      a plurality of carriers coupled to the base, a first one of the carriers being operatively connected to a drive member for moving the first carrier in a first direction, the first carrier having at least a plurality of bristles and a second one of the carriers having an elastomeric cleaning element extending outwardly therefrom, the elastomeric cleaning element forming an elongate, non-linear wall having a plurality of inflection points;
   wherein the elastomeric cleaning element stretches and compresses when driven by the drive member.

2. The powered toothbrush of claim 1, wherein the elastomeric wall has a shape selected from the group consisting of zigzag and serpentine.

3. The powered toothbrush of claim 1, wherein said elastomeric cleaning element has a smooth or rough surface.

4. The powered toothbrush of claim 1, wherein the elastomeric cleaning element is operatively connected to the drive member and moves when driven by the drive member.

5. The powered toothbrush of claim 1, wherein the elastomeric cleaning element extends outwardly from the second carrier and the elastomeric cleaning element moves in a plane substantially parallel to the first direction when driven by the drive member.

6. A powered toothbrush comprising:
   a handle portion having a neck at one end thereof and being adapted to receive a battery in an interior compartment formed therein; and
   a head coupled to the neck, the head comprising:
      a base;
      a first carrier coupled to the base having a disc shape permitting rotational movement of the first carrier about a center portion of the disc, the first carrier having a cleaning element extending therefrom;
      a drive member operatively coupled to the first carrier for rotating the first carrier, and
      a second carrier coupled to the base and having a non-circular shape, the second carrier having an elastomeric wall extending outwardly from a face thereon and substantially extending across the width of the face;
   wherein the elastomeric wall is non-linear and has a plurality of bends.

7. The powered toothbrush of claim 6, wherein the elastomeric wall is operatively coupled to the drive member.

8. The powered toothbrush of claim 7, wherein the elastomeric wall extends outwardly in a direction substantially perpendicular from a face of the second carrier, and the elastomeric wall moves in a plane substantially parallel with the face when driven by the drive member.

9. A powered toothbrush comprising:
   a handle portion having a neck at one end thereof and being adapted to receive a battery in an interior compartment formed therein; and
   a head coupled to the neck, the head comprising:
      a base;
      a first carrier coupled to the base having a disc shape permitting rotational movement of the first carrier about a center portion of the disc, the first carrier having a cleaning element extending therefrom;
      a drive member operatively coupled to the first carrier for rotating the first carrier; and
      a second carrier coupled to the base and having a non-circular shape, the second carrier having an elastomeric wall extending outwardly therefrom;
   wherein the elastomeric wall stretches and compresses when driven by the drive member.

10. A powered toothbrush comprising:
    a handle portion having a neck at one end thereof and being adapted to receive a battery in an interior compartment formed therein; and
    a head coupled to the neck, the head comprising:
       a base;
       a first carrier coupled to the base having a disc shape permitting rotational movement of the first carrier about a center portion of the disc, the first carrier having a cleaning element extending therefrom;

a drive member operatively coupled to the first carrier for rotating the first carrier; and a second carrier coupled to the base and having a non-circular shape, the second carrier having an elastomeric wall extending outwardly therefrom;

wherein the elastomeric wall is operatively coupled to the drive member, the elastomeric wall comprises a first end portion, an opposite second end portion, and an intermediate portion extending therebetween, and the intermediate portion is detached from the second carrier for sliding movement with respect to the second carrier when driven by the drive member.

11. The powered toothbrush of claim 10, wherein the first end portion is operatively coupled to the drive member and the second end portion is attached to the first carrier.

12. The powered toothbrush of claim 10, wherein the first and second end portions are operatively coupled to the drive member.

13. A powered toothbrush comprising:
a handle portion adapted to receive a battery in an interior compartment formed therein;
a head coupled to the handle portion, the head comprising;
a drive feature;
a face having a width;
a first carrier disposed on a first portion of the face and operatively connected to the drive feature for being driven by the drive feature, the first carrier having a plurality of first cleaning members extending outwardly therefrom; and
an upstanding elastomeric wall disposed on a second portion of the face and extending outwardly from the face, the upstanding elastomeric wall substantially extending across the width of the face;
wherein the upstanding elastomeric wall is non-linear and has a plurality of bends wherein the non-linear, upstanding elastomeric wall includes a plurality of segments separated by the bends that each substantially extend across the width of the face.

14. The powered toothbrush of claim 13, wherein the upstanding elastomeric wall is operatively connected to the drive feature and moves when being driven by the drive feature.

15. A powered toothbrush comprising:
a handle portion;
a drive feature;
a head coupled to the handle portion and the drive feature and having a face; and
a stretchable and compressible elastomeric polishing element extending outwardly from the face, the elastomeric polishing element stretching and compressing in a direction substantially parallel to the face during operation of the toothbrush when driven by the drive feature.

16. The toothbrush of claim 15, wherein the elastomeric polishing element is a wall.

17. The toothbrush of claim 15, wherein the elastomeric polishing element traverses a non-linear path between a first end portion and a second end portion thereof.

18. The toothbrush of claim 17, wherein the non-linear path comprises a plurality of inflection points.

19. The toothbrush of claim 15, wherein a first end portion of the elastomeric polishing element is attached to a movable carrier.

20. The toothbrush of claim 19, wherein a second end portion of the elastomeric polishing element opposite the first end portion is attached to a movable carrier.

21. A toothbrush comprising:
a handle portion;
a head coupled to the handle portion and having a face;
a platform disposed on the face; and
an elongate, elastomeric, upstanding wall extending outwardly from the platform in a first direction substantially perpendicular to the platform, the elongate, elastomeric upstanding wall comprising;
a first end portion;
an opposite second end portion; and
a middle portion between the first and second end portions, the middle portion detached from the platform and translatable in a second direction substantially perpendicular to the first direction.

22. The toothbrush of claim 21, wherein the second end portion is translatable in a direction substantially parallel to the platform.

23. The toothbrush of claim 21, wherein the elongate, elastomeric, upstanding wall is longitudinally stretchable and compressible between the first end portion and the second end portion.

24. The toothbrush of claim 21, wherein the elongate, elastomeric, upstanding wall traverses a non-linear path between the first end portion and the second end portion.

25. The toothbrush of claim 24, wherein the non-linear path comprises a plurality of inflection points while in a relaxed configuration.

26. The toothbrush of claim 21, wherein the first end portion is attached to a first movable carrier.

27. The toothbrush of claim 26, wherein the second end portion is attached to a second movable carrier.

28. A toothbrush comprising:
a handle portion;
a head coupled to the handle portion and having a face;
a platform disposed on the face; and
an elongate, elastomeric, upstanding wall extending outwardly from the platform in a first direction substantially perpendicular to the platform, the elongate, elastomeric upstanding wall comprising:
a first end portion;
an opposite second end portion; and
a middle portion between the first and second end portions, the middle portion detached from the platform and translatable in a second direction substantially perpendicular to the first direction; and
a movable carrier comprising the platform, the movable carrier being movable with respect to the head.

* * * * *